US00PP14990P2

(12) United States Plant Patent
Olesen et al.

(10) Patent No.: US PP14,990 P2
(45) Date of Patent: Jul. 6, 2004

(54) MINIATURE ROSE PLANT 'POULHI006'

(50) Latin Name: *Rosa hybrida*
Varietal Denomination: POULhi006

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/268,204

(22) Filed: Oct. 9, 2002

(51) Int. Cl.[7] ..... A01H 5/00
(52) U.S. Cl. ..... Plt./118
(58) Field of Search ..... Plt./118

*Primary Examiner*—Anne Marie Grunberg
*Assistant Examiner*—June Hwu

(57) ABSTRACT

A new miniature rose which has abundant, yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Classification: Botanical: *Rosa hybrida*. Denomination: 'POULhi006'. Commercial: Miniature.

SUMMARY OF THE INVENTION

The present discovery constitutes a new and distinct variety of a miniature pot rose plant which was discovered in a cultivated area. The mutation resulted from an unnamed, non-patented seedling. The new rose variety resulted from a naturally occurring mutation of unknown causation on a branch of the unnamed seedling.

The rose plant of the present discovery has a unique combination of characteristics which are outstanding in the new variety and which distinguish it from the original rose as well as all other varieties which we are aware of. For example, the new variety has:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULhi006' from all other varieties of which we are aware.

The resulting mutation was selected and evaluations were conducted on the resulting rose plants in a controlled environment.

Asexual reproduction of 'POULhi006' by cuttings and traditional budding was first done by L. Pernille and Mogens N. Olesen in their nursery in Fredensborg, Denmark in 2000. This initial and other subsequent propagations conducted in controlled environments have demonstrated that the characteristics of 'POULhi006' are true to type and are transmitted from one generation to the next.

BRIEF DESCRIPTION OF THE DRAWINGS

The accompanying color illustration shows as true as is reasonably possible to obtain in color photographs of this type, the typical characteristics of the buds, flowers, leaves, and stems of 'POULhi006'. Specifically, illustrated in SHEET 1:

1. Stem showing a single, partially opened flower including its leaves and peduncle;
2. Flower bud as sepals unfold and an open flower;
3. Flower petals, detached;
4. Sepals, receptacle, and pedicel;
5. Two bare stems exhibiting thorns;
6. Leaves.

DETAILED DESCRIPTION OF THE VARIETY

The following is a description of 'POULhi006', as observed in its growth in a field nursery in Jackson County, Oreg. Observed plants are 3 year budded plants. Color references are made using The Royal Horticultural Society (London, England) Colour Chart, 1995, except where common terms of color are used.

For a comparison, several physical characteristics of the rose variety 'POULhi001', a rose variety from the same inventors, described and illustrated in U.S. Plant Pat. No. 13,493 granted Jan. 21, 2003 is compared to 'POULhi006', in Chart 1.

CHART 1

| | 'POULhi006' | 'POULhi001' |
|---|---|---|
| Petal count | 10 to 15. | 38 to 45. |
| Petal color, upper surface. | Yellow Group 11C. | Yellow-Orange Group 15A. |
| Petal color, lower surface. | Yellow Group 11C. | Yellow-Orange Group 15C. |

Parent: Mutation from an unnamed seedling.

FLOWER AND FLOWER BUD

Blooming habit: Continuous.
Flower bud:
*Size.*—Upon opening, 35 to 40 mm in length from base of receptacle to end of bud.
*Bud form.*—Pointed ovoid.

*Bud color.*—As sepals unfold, Yellow-Orange Group 18A. At ¼ opening, Yellow-Orange Group 18A.

*Sepals.*—Upper surface is Green Group 143A. Lower surface is Green Group 143B. Weak foliaceous appendages on three of the five sepals. Surfaces of sepals slightly pubescent. Stipitate glands are present on sepal edges and undersides. Shape: Sepal apex is cirrhose. Base is flat, sepals are attached to the receptacle. Size: 25 to 30 mm long×7 mm wide.

*Receptacle.*—Surface: Smooth. Shape: Urn-shaped. Size: 7 mm (h)×7 mm (w). Color: Yellow-Green Group 145A.

*Peduncle.*—Surface: With fragrant stipitate glands. Length: 40 to 55 mm average length. Color: Yellow-Green Group 145A. Strength: Strong.

*Borne.*—Singly.

*Anthocyanin.*—Greyed-Red Group 178B.

Flower bloom:

*Fragrance.*—Light.

*Duration.*—As a pot plant, flowers last from 7 to 10 days. Petals fall cleanly away from plant.

*Size.*—Average flower diameter is 80 mm when open.

*Form.*—Shape of flower when viewed from the side: Upon opening, upper part: Convex. Upon opening, lower part: Flattened convex. Open flower, upper part: Flattened convex. Open flower, lower part: Concave.

*Petalage.*—Average range: 10 to 15 petals under normal conditions with 4 to 6 petaloids.

Color:

*Upon opening, petals.*—Outermost petals: Outer side: Yellow-Orange Group 16D. Inner side: Yellow-Orange Group 16C. Innermost petals: Outer side: Yellow-Orange Group 16C. Inner side: Yellow-Orange Group 16C.

*Upon opening, basal petal spots.*—Outermost petals: Outer side: Yellow Group 12B. Inner side: Yellow Group 12B. Innermost petals: Outer side: Yellow Group 12B. Inner side: Yellow Group 12B.

*After opening, petals.*—Outermost petals: Outer side: Yellow Group 11C. Inner side: Yellow Group 11C. Innermost petals: Outer side: Yellow Group 11C. Inner side: Yellow Group 11C.

*After opening, basal petal spots.*—Outermost petals: Outer side: Yellow Group 12B. Inner side: Yellow Group 12B. Innermost petals: Outer side: Yellow Group 12B. Inner side: Yellow Group 12B.

General tonality: On open flower Yellow-Green Group 16B. No change in the general tonality at the end of the 5th day. Afterwards, general tonality is Yellow Group 11C.

Petals:

*Petal reflex.*—Strong.

*Petal edge.*—Entire.

*Size.*—40 mm (l)×42 mm (w).

*Texture.*—Smooth.

*Shape.*—Apex is rounded, base is rounded.

*Petaloids.*—Quantity: 4 to 5. Size: 40 to 50 mm long; 10 to 30 mm wide. Color: Yellow Group 11C on both upper and lower surfaces.

*Thickness.*—Average.

*Arrangement.*—Formal.

Reproductive organs:

*Pistils.*—Length: 7 to 9 mm long. Quantity: 80.

*Pollen.*—None observed.

*Anthers.*—Size: 8 mm long. Color: Yellow Group 10C. Quantity: 133.

*Filaments.*—Color: Yellow Group 11A. Length: 2 mm.

*Stigmas.*—Slightly inferior in location to anthers. Color: Yellow Group 10C.

*Styles.*—Color: Yellow Group 10D, with intonations of Red Group 53C.

*Seed formation.*—Hips: Not observed.

PLANT

Plant growth: Vigorous, bushy. When grown as a 12 cm pot plant, the average height of the plant itself is 40 to 60 cm and the average width is 40 cm.

Stems:

*Color.*—Young wood: Yellow-Green Group 144A. Older wood: Yellow-Green Group 144A.

*Prickles.*—Incidence: 1 thorn per 10 cm of stem. Size: Average length: 5 mm. Color: Greyed-Yellow Group 161A. Shape: Concave.

*Surface.*—Young wood: Smooth. Older wood: Smooth.

Plant foliage: Normal number of leaflets on normal leaves in middle of the stem: 5 leaflets.

*Leaf size.*—Compound leaves are 120 mm (l)×75 mm (w).

*Quantity.*—Average.

*Texture.*—Smooth.

*Color.*—Upper Leaf Surface: Green Group 137A. Lower Leaf Surface: Green Group 138B. Juvenile foliage: Upper Leaf Surface: Green Group 137C. Lower Leaf Surface: Yellow-Green Group 144A.

Plant leaves and leaflets:

*Stipules.*—Size: 10 to 13 mm. Color: Yellow-Green Group 144A.

Stipitate glands: Present on margins.

*Petiole.*—Length: 12 to 22 mm. Color: Yellow-Green Group 144B. Underneath: Yellow-Green Group 144B. Margins: With stipitate glands.

*Rachis.*—Color: Yellow-Green Group 144B. Underneath: Yellow-Green Group 144B. Margins: With stipitate glands.

*Leaflet.*—Edge: Serrate. Size: The terminal leaflet is 42 mm in length by 28 mm wide. Shape: Ovate. Apex is acute; base is rounded. Surface Texture: Smooth. Glossiness: Moderate. Arrangement: Odd pinnate. Venation: Reticulate.

Disease resistance: Average resistance to mildew, black spot, and Botrytis under normal growing conditions in Jackson County, Oreg.

What is claimed is:

1. A new and distinct variety of rose plant of the miniature class, substantially as herein illustrated and described as a distinct and novel rose variety due to its abundant, yellow flowers, vigorous growth, compact habit, suitability for production from softwood cuttings in pots, and durable flowers and foliage which make the variety suitable for distribution in the floral industry.

* * * * *

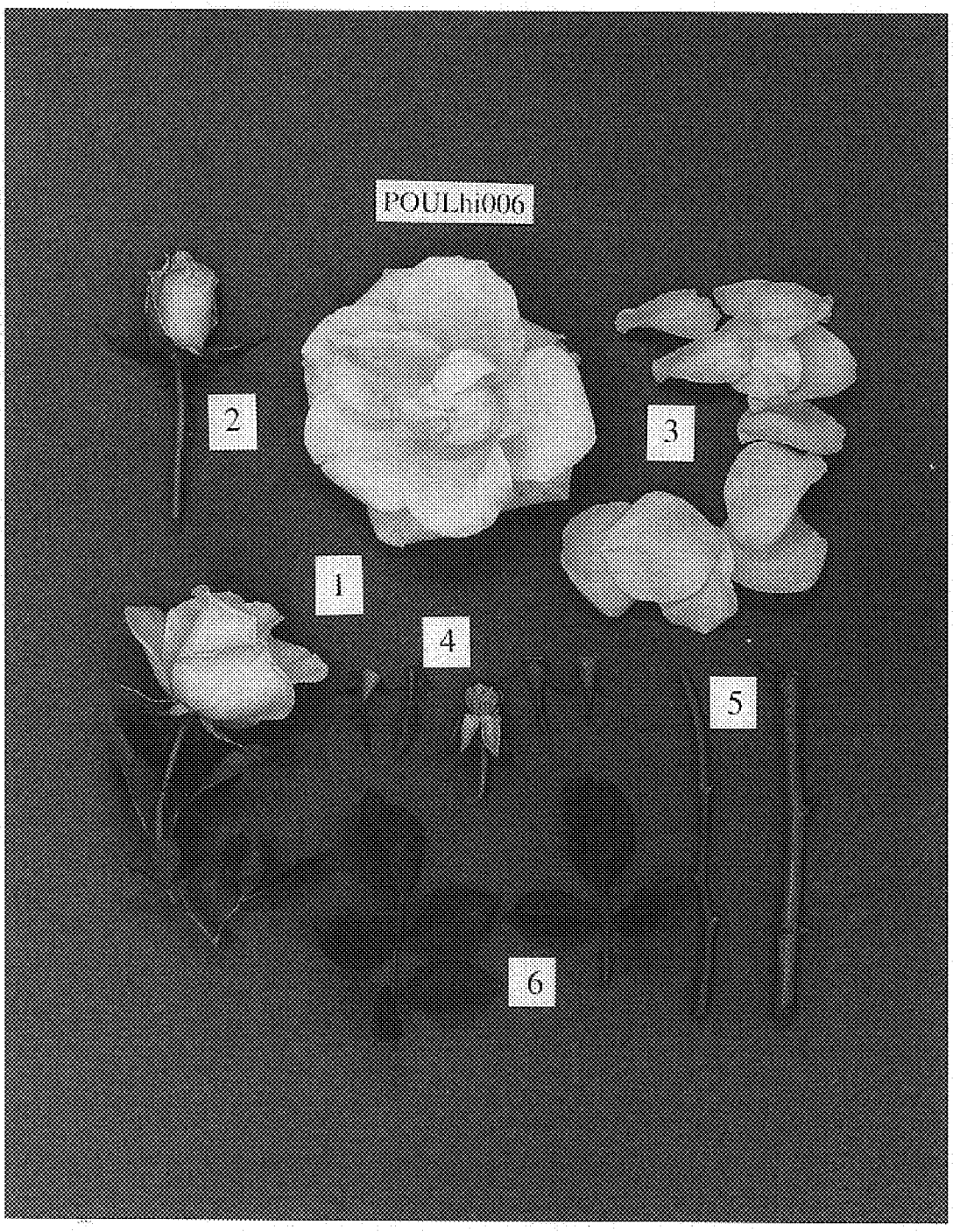
POULhi006
2
3
1
4
5
6